United States Patent [19]

Heller et al.

[11] Patent Number: 4,764,364

[45] Date of Patent: Aug. 16, 1988

[54] METHOD OF PREPARING BIOERODIBLE POLYMERS HAVING PH SENSITIVITY IN THE ACID RANGE AND RESULTING PRODUCT

[75] Inventors: Jorge Heller, Woodside; Donald W. H. Penhale, Menlo Park; Steve Y. Ng, San Francisco, all of Calif.

[73] Assignee: S R I International, Menlo Park, Calif.

[21] Appl. No.: 833,215

[22] Filed: Feb. 25, 1986

[51] Int. Cl.$^4$ .................... A61K 9/22; A61K 31/765; C08G 65/28

[52] U.S. Cl. .................... 424/78; 523/105; 528/392; 424/426; 514/950; 514/964; 514/866

[58] Field of Search .................... 528/392; 424/19, 22, 424/78, 426; 514/866, 950, 964; 523/105; 128/260

[56] References Cited

U.S. PATENT DOCUMENTS

| | | |
|---|---|---|
| 4,093,709 | 6/1978 | Choi et al. .................... 424/19 |
| 4,131,648 | 12/1978 | Choi et al. .................... 424/19 |
| 4,138,344 | 2/1979 | Choi et al. .................... 424/19 |
| 4,180,064 | 12/1979 | Heller et al. .................... 424/19 |
| 4,180,646 | 12/1979 | Choi et al. .................... 424/19 |
| 4,261,969 | 4/1981 | Heller .................... 424/22 |
| 4,304,767 | 12/1981 | Heller et al. .................... 424/19 |
| 4,489,056 | 12/1984 | Himmelstein et al. .................... 424/22 |
| 4,590,190 | 5/1986 | Saito et al. .................... 514/221 |

*Primary Examiner*—Ronald W. Griffin
*Attorney, Agent, or Firm*—Edward B. Gregg; Urban H. Faubion; John Y. Chen

[57] ABSTRACT

Biodegradible polymers are provided which may contain a biologically active substance, e.g. a drug such as insulin, which is released over a period of time as the polymer erodes when in contact with a body fluid. The polymer contains an amine functionality whereby it erodes faster at low acid pH's than at higher acid pH's. As an example, the polymer may contain insulin and may contain or may have an encapsulating hydrogel containing glucose oxidase. As the blood sugar level of a diabetic person rises, e.g., afte a meal, glucose diffuses into the polymer or hydrogel and is converted to gluconic acid which lowers the pH, and accelerates erosion and the release of insulin.

23 Claims, 3 Drawing Sheets

METHOD OF PREPARING BIOERODIBLE POLYMERS HAVING PH SENSITIVITY IN THE ACID RANGE AND RESULTING PRODUCT

BACKGROUND OF THE INVENTION

1. Field of the Invention

This invention relates to bioerodible polymers containing a biologically active substance which is released when the polymer is brought into contact with a body fluid, thus releasing the biologically active material gradually and over a period of time. More particularly, this invention relates to such products in which the bioerodible polymer is sensitive to acidic media whereby control of the rate of erosion, and hence the rate of release of the biologically active substance can be controlled.

2. Description of the Prior Art

In U.S. Pat. No. 4,093,709 there are described bioerodible polymers intended to contain drugs for release as the polymer is eroded by contact with body fluids, such polymers being poly(ortho esters) or polycarbonates. A typical such polymer has the formula

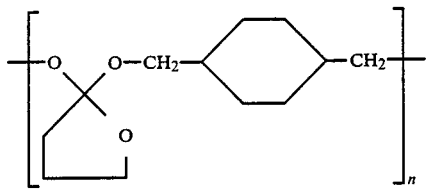

See also U.S. Pat. Nos. 4,131,648; 4,138,344 and 4,180,646.

Another class of bioerodible polymers suitable for the same purpose is described in U.S. Pat. No. 4,304,767 (the '767 Patent). These polymers are formed by a condensation reaction of a ketene acetal with a polyol and they have certain advantages over those of the U.S. Pat. No. 4,093,709, such as the fact that their production is not accompanied by the formation of low molecular weight by-products such as alcohol and the reaction proceeds rapidly and at ambient temperature. The absence of formation of small molecular weight by-products enables one to produce dense crosslinked materials incorporating a drug.

It has been proposed to employ bioerodible polymers for the gradual release of drugs, such polymers being sensitive to the pH of the ambient medium. See, for example, a paper by Heller et al. in the Journal of Applied Polymer Science, Vol. 22, pp. 1991–2009 (1978). These polymers are partial esters of methyl vinyl ether-maleic anhydride copolymers which have been reacted with alcohols to form polymers that contain both carboxylic acid and carboxylic ester functionalities.

In these polymers, the size of the alkyl group in the ester functionality determines the rate at which the polymer erodes at a constant external pH. Most importantly, any particular polymer exhibits a very pronounced dependence of erosion on the external pH and even very small changes in this external pH have a very large effect on rate of polymer erosion.

An approach to utilizing this methodology is described in a paper by Heller and Trescony in Journal of Pharmaceutical Sciences, Vol. 68, pp. 919–921 (1979). A polymer similar to those of the cited Heller and Trescony paper containing a drug is coated with a hydrogel containing urease. When exposed to a solution containing urea, the urease in the hydrogel acts on the urea, which infuses into the hydrogel, thus releasing ammonium bicarbonate and ammonium hydroxide. This accelerates erosion of the bioerodible polymer and hence accelerates release of the drug, e.g., hydrocortisone.

SUMMARY OF THE INVENTION

It is an object of the invention to provide superior bioerodible polymers which are pH sensitive and respond to media having an acidic pH.

It is a further object of the invention to provide products incorporating a bioerodible polymer containing a biologically active ingredient which is released as the polymer undergoes erosion, such product being sensitive to acid pH, whereby under acid conditions the rate of erosion of the polymer and release of the biologically active material is controlled by the pH.

The above and other objects will be apparent from the ensuing description and the appended claims.

We have discovered that bioerodible polymers such as those described and claimed in U.S. Pat. No. 4,304,767 can be modified to render them highly pH sensitive in a desired acid range whereby the rate of erosion, hence the rate of drug release, can be controlled by the pH of the surrounding medium. Such modification is brought about by including in the polymer an amine functionality. This method is applicable also to other bioerodible polymers such as those of U.S. Pat. Nos. 4,093,709; 4,131,648; 4,138,344 and 4,180,646. The preferred polymers are those of U.S. Pat. No. 4,304,767 (the '767 Patent).

DETAILED DESCRIPTION OF THE INVENTION

The Preferred Bioerodible Polymers

Figure 1:
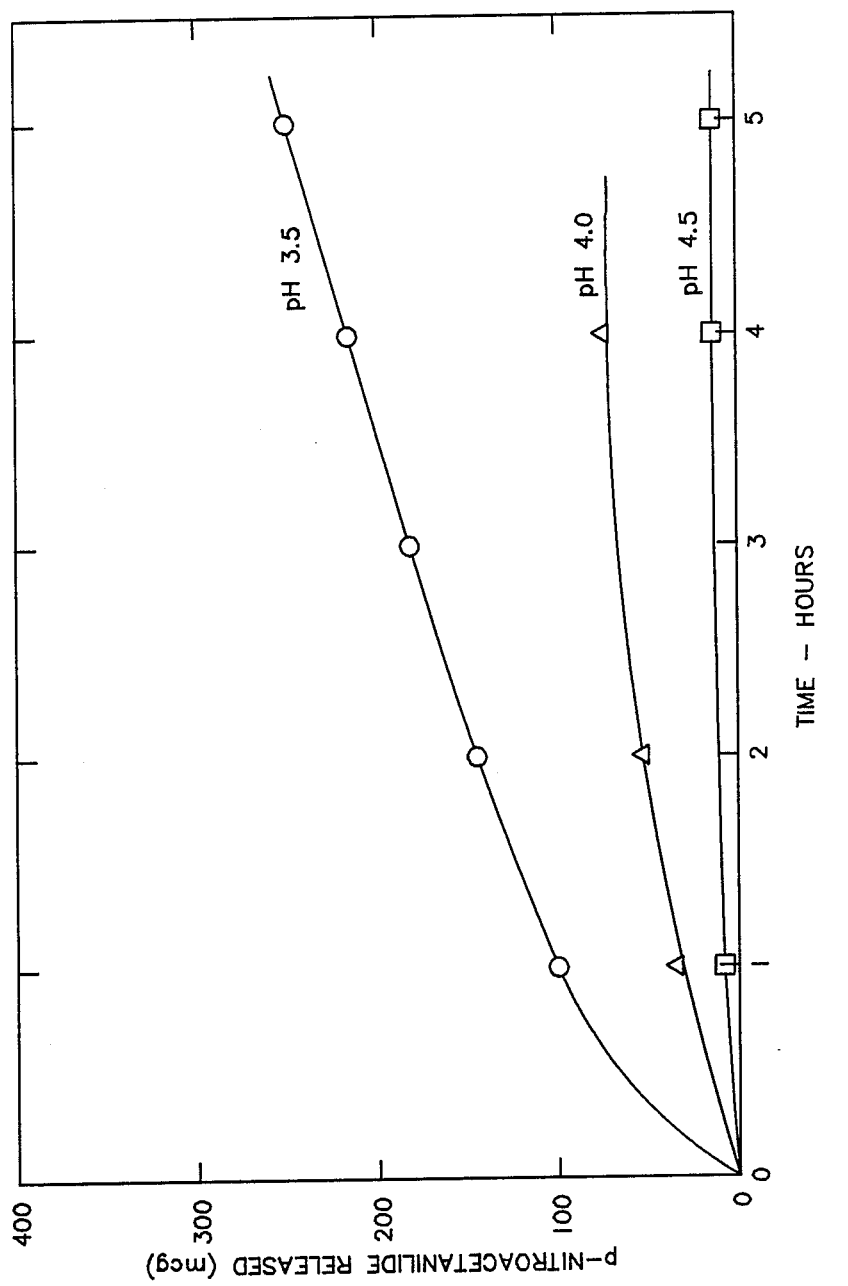

The preferred bioerodible polymers are those described in U.S. Pat. No. 4,304,767, such description being incorporated herein by reference in its entirety. Briefly stated, two types of ketene acetal monomers are described as follows:

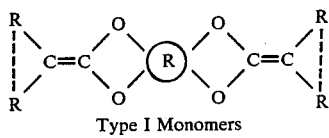

Type I Monomers

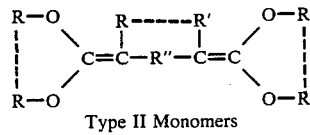

Type II Monomers

The Type I monomers are condensed with polyols to afford Type I polymers which, when the polyol is a diol $R(OH)_2$ have the linear structure

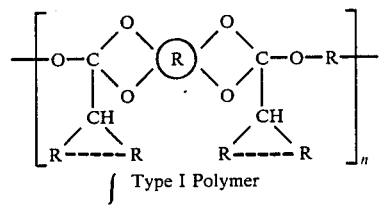

Type I Polymer

If the polyol is a triol or polyol of higher functionality, or if a ketene acetal having a functionality of three or more is used, then the Type I polymer is a cross-linked polymer.

The Type II monomers, when reacted with diols R(OH)₂, afford Type II linear polymers, having the structure

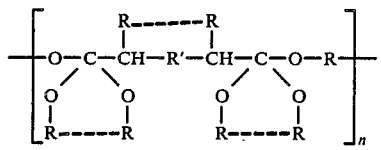

Type II Polymer

As in the case of the Type I polymers if the polyol or the ketene acetal has a higher functionality than two, crosslinking occurs.

As starting materials for the preferred embodiment of the invention, any of the ketone acetals of Type I or Type II and any of the polyols described in the '767 Patent may be employed. For example, any of the diketene acetals described in the literature which is cited at column 4, line 33 to column 5, line 3 of the '767 Patent may be used and any of the polyols described in column 6, line 52 to column 7, line 66, may be used provided they are compatible with the purpose of the present invention, namely the introduction of an amine functionality into the polymer and the endowment of pH sensitivity in the acid range to the polymer. Type I diketene acetals are preferred.

We have found that by incorporating in the poly(ortho esters) of the '767 Patent an amine group, the pH sensitivity of the polymers in the acid range is altered. That is, the rate of erosion of the polymer, hence the release of a biologically active substance in the polymer, can be modified and controlled.

An amine group can be introduced into the polymer in various ways such as the following:

As stated above and as described in the 767 Patent, the Type I and Type II polymers are prepared by condensing a Type I or a Type II diketene acetal (or a ketene acetal of higher functionality) with a polyol. The amine functionality of the present invention may be incorporated in the ketene acetal or in the polyol or in both, such that when the ketene acetal and the polyol are reacted a polymer results which contains one or more types of amine groups.

If the amine group is incorporated in the ketene acetal, it may be incorporated, for example, in the R group of Type I or in the R" group of Type II monomer. Preferably, however, the amine group is incorporated in a prepolymer which is prepared by reacting a ketene acetal with a diol R(OH)₂ in which R contains an amine group. The prepolymer has the general formula 3 set forth in the reaction scheme below.

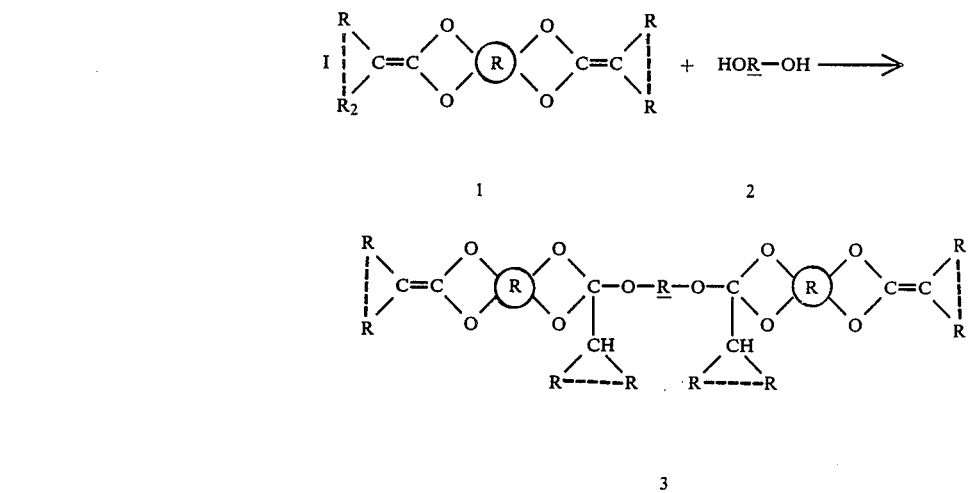

This prepolymer is then reacted with a polyol $R_x(OH)_n$ to produce a polymer which, if n=3 or more, is cross linked

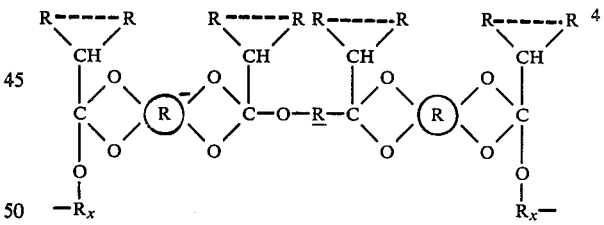

If (as is preferred) the polyol in reaction I is a triol or a polyol of higher functionality, the polymer 4 is crosslinked. Polymer 4 is written for a triol R₆(OH)₃. The formula will be apparent for higher polyols and for diols.

The preparation of such a prepolymer is preferred because a biologically active agent can be conveniently incorporated in the prepolymer and will, therefore, be incorporated in the polymer 4. This is especially advantageous where the polymer is crosslinked because the biologically active agent may be uniformly mixed with or dissolved in the prepolymer, hence will be uniformly incorporated in the polymer.

If the ketene acetal is of Type II, the same procedure (forming a prepolymer containing an amine group in the linking group which links two ketene acetal moieties) may be used. The prepolymer will have the structure

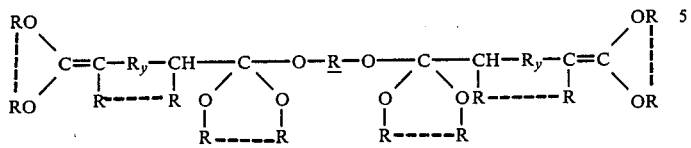

The polymer will have the structure

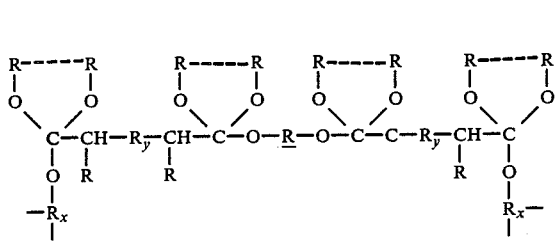

and will be crosslinked if the polyol $R_x(OH)_n$ used in the polymerization reaction is a tri- or higher polyol.

Alternatively a Type I or Type II di- (or higher) ketene acetal may be polymerized with a polyol which contains an amine group. The polymer will be of Type I or Type II as shown above but with an amine group incorporated in the $R_x$ group derived from the polyol.

In the formulae above the R's may be the same or different, and they may be hydrogen or essentially hydrocarbon groups (with amine functionality if desired). The group ®· is a quadrivalent group which is essentially hydrocarbon. $\underline{R}$, $R_x$ and $R_y$ are bivalent essentially hydrocarbon groups, preferably having an amine functionality in the case of R. $R_x$ also preferably contains an amine functionality. The groups R, ®, $R_x$ and $R_y$ may contain hetero atoms (e.g. nitrogen in the form of an amine group) provided the hetero atom or group does not interfere with polymerization, does not interfere with erosion and does not interfere with the intended pH sensitivity of the polymer. R - - - R signifies that the R's may be separate groups or may together form parts of a cyclic group.

The following specific examples will serve further to illustrate the practice of the present invention.

EXAMPLE 1

The diketene acetal 3,9-bis (ethylidene 2,4,8,10-tetraoxaspiro [5,5] undecane ($\underline{7}$) was reacted with the linker N-butyldiethanolamine (8) to form a prepolymer $\underline{9}$ which was then reacted with the polyol $\underline{10}$ to form a crosslinked polymer $\underline{11}$. The reaction scheme was as follows:

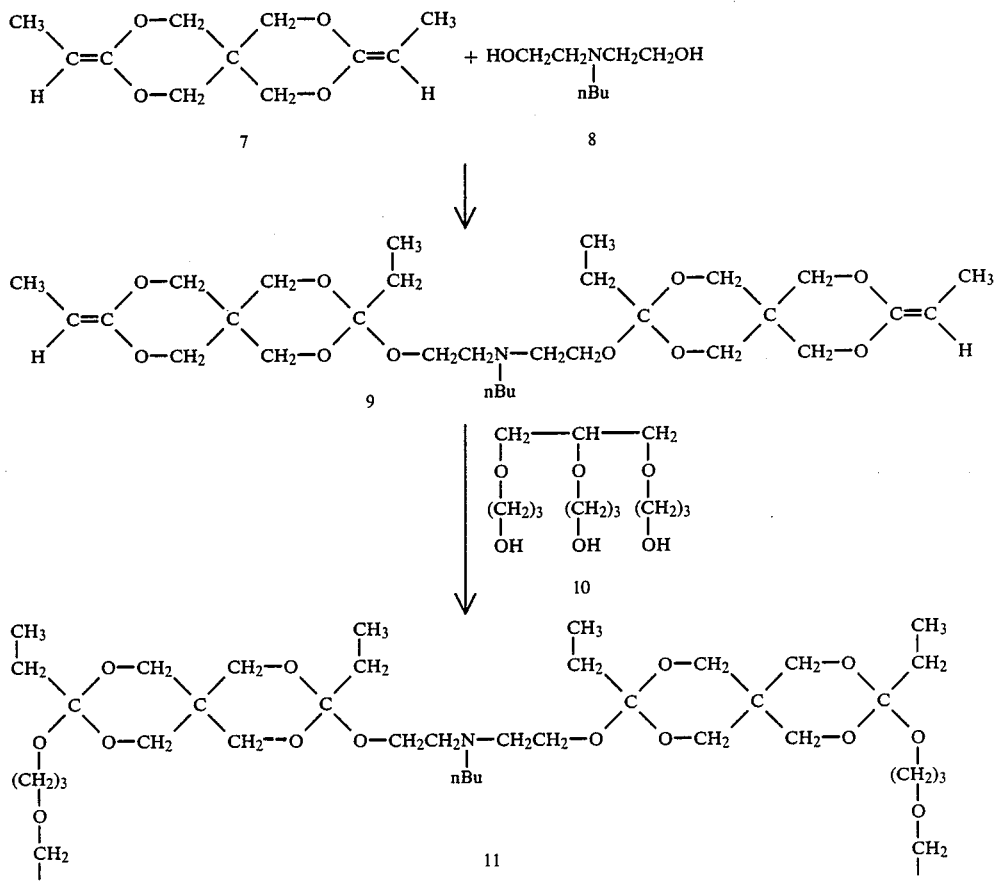

The reactions were carried out as follows: in a 120 ml round bottom flask equipped with a paddle stirrer and argon inlet and outlet was placed 15 g (0.0703 mole) of 7 and 5.67 g (0.0352 mole) of 8. The reaction was initiated by addition of 0.1 ml of iodine in pyridine solution (0.1 g/100 ml). After one hour the reaction is complete.

Crosslinked polymers were prepared by taking 4 grams of the liquid prepolymer 11 and adding 1.5 g (0.0054 mole) of 10. After the viscous mixture is shaped to the desired form, it is cured at 70° C. for 18 hours.

EXAMPLE 2

Using the procedure described in Example 1, 15 g (0.0703 mole) of 7 was reacted with 4.19 g (0.0352 mole) methyldiethanolamine. The resulting prepolymer was crosslinked with triethanolamine.

EXAMPLE 3

Using the procedure described in Example 1, 15 g (0.0703 mole) of 7 was reacted with 5.17 g (0.0352 mole) of 3-diethylamino-1,2-propanediol. The resulting prepolymer was crosslinked with tri-isopropanolamine.

EXAMPLE 4

Using the procedure described in Example 1, 15 g (0.0703 mole) of 7 was reacted with 6.58 g (0.0352 mole) of cyclohexyl diethanolamine. The resulting prepolymer was crosslinked with 1,2,6-hexanetriol.

EXAMPLE 5

Using the procedure described in Example 1 15 g (0.0703 mole) of 7 are reacted with 4 g (0.0352) mole) of 1,6-hexanediol to form a prepolymer which is crosslinked with triethanolamine.

EXAMPLE 5a

Using the procedure described in Example 1, 15 g (0.0703 mole) of 7 are reacted with 8.33 g (0.0703 mole) of methyl diethanolamine. In this case, a high molecular weight, linear polymer is obtained.

EXAMPLE 6

In vitro testing of erosion and drug release

A marker drug, p-nitroacetanilide was mixed into the prepolymer to give a concentration of 2 wt%. After adding the crosslinker, the viscous mixture was extruded into a polyethylene tube having an inside diameter of 0.25 in. and cured at 70° C. for 18 hours. (However, if a sensitive therapeutic agent is used, lower cure temperatures and longer reaction times can be used.)

After the polymer has cured, the tube is sliced to produce disks having an approximate thickness of 0.030 in. and the outer shell from the polyethylene tube is removed. The disks are put into stainless steel mesh bags which are attached to stainless steel wires and vertically agitated at the rate of one stroke per second in 30 mls. of the appropriate buffer solutions in 40 ml. test tubes. The buffer solutions are made from citric acid and sodium dibasic phosphate for all ranges of pH. The test tubes are thermostatically controlled at 37° C.

The buffer solutions are changed and analyzed at the appropriate time intervals commensurate with the rate of release of the p-nitroacetanilide marker. The analyses are performed on a Model 554 Perkin Elmer spectrophotometer by reading the lambda max absorption at 318 nm and concentrations are calculated from a standard absorption curve.

EXAMPLE 7

Figure 4:
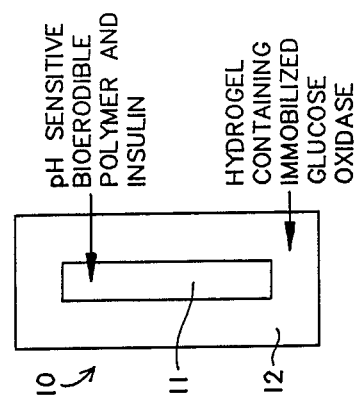

Preparation of Hydrogel Device of FIG. 4

A disk containing insulin dispersed in the amine-containing poly(ortho ester) is prepared and a small locking forceps is affixed to the edge of each polymer disk so that it can be manipulated without touching the surfaces during the immobilized enzyme-coating procedure. A 30% aqueous solution of bovine serum albumin is prepared, and 1 g of glucose oxidase is added to 10 ml of this solution. After quick stirring to dissolve the glucose oxidase, the solution is chilled in an ice bath. Each disk is held horizontally by the attached forceps, and 1 drop of glucose oxidase solution is added to the upper disk face. The disk is quickly rotated, and a drop is added to the opposite face. Similarly, 1 drop of 25% aqueous glutaraldehyde is added to each face. One minute after the glutaraldehyde addition, the coating has gelled sufficiently to allow the disks to be hung vertically. This procedure immobilizes the glucose oxidase in the hydrogel.

After standing in air for 15 min., the coated disks are immersed in cold, deionized water for 15 min. in 0.1M glycine for 15 min, and in pH 5.75 phosphate buffer for 2 hr. Finally, they are immersed in fresh pH 5.75 phosphate buffer for 4 hr.

Figure 2:
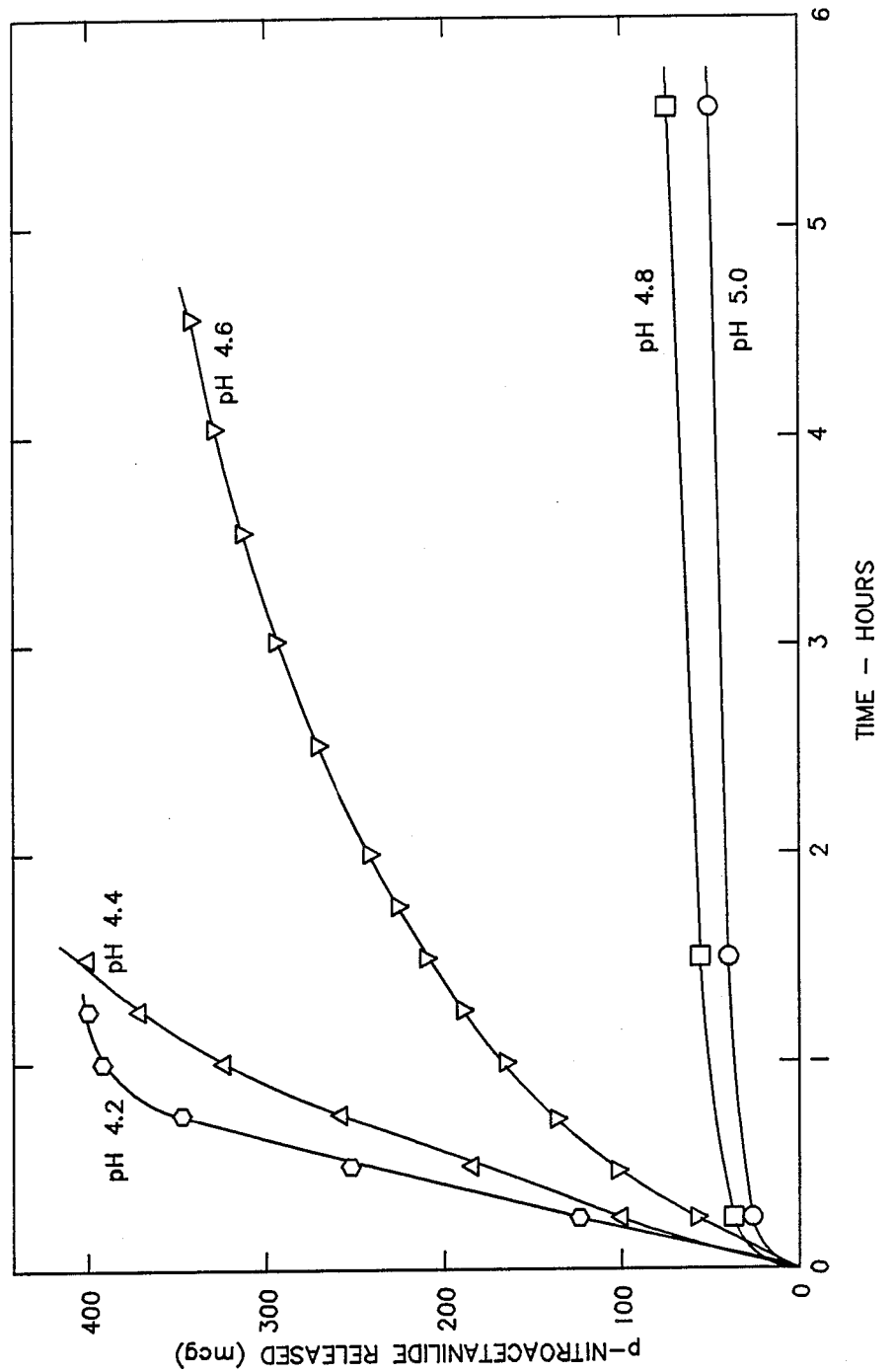
Figure 3:
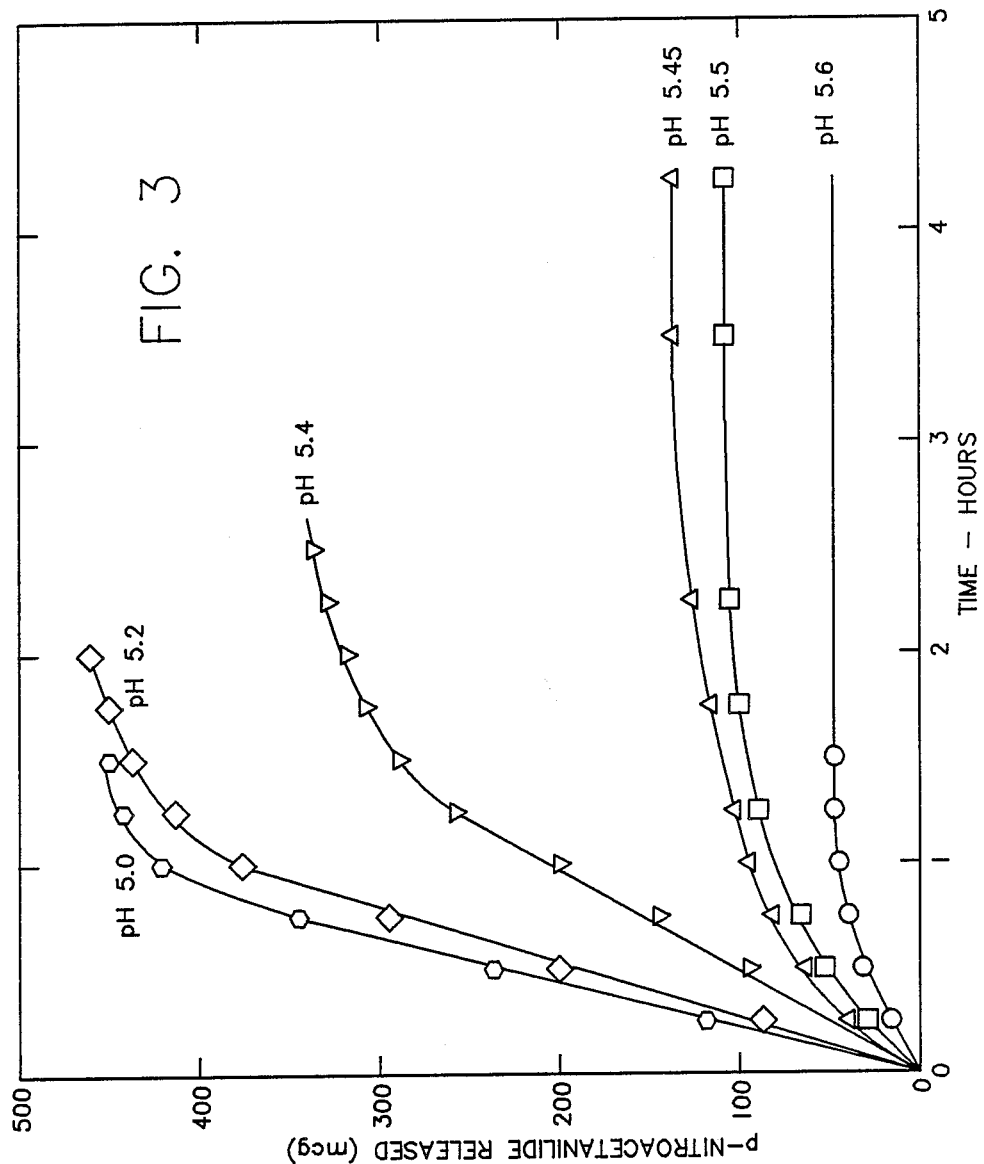

Referring now to FIGS. 1, 2 and 3 of the drawings, the test results of the procedure of Example 6 as applied to the polymers of Examples 1, 2 and 3 respectively are shown. The degree of erosion (as measured by the p-nitroacetanilide concentration) is plotted against time. The polymer of Examples 1, 2 and 3 were used with p-nitroacetanilide and the results are plotted in FIGS. 1, 2 and 3, respectively. It will be seen that with polymer 11 (Example 1) the rate of erosion was least at pH 4.5; it was greater at pH 4.0; and it was still greater at pH 3.5.

With the polymer of Example 2 the rate of erosion was low at pH 5.0 and 4.8, much greater at pH 4.2 and very much greater at pH 4.4 and 4.2. This is believed to be due to the fact that the polymer contained two amine functionalities, one in the linking group of the prepolymer and the other in the crosslinking moieties.

Similar results are shown in FIG. 3 (Example 3).

Referring now to FIG. 4, a device is shown which is generally designated by the reference numeral 10. It comprises a polymer 11 encased in a hydrogel layer 12. The polymer 11 is that of the present invention and it contains a drug or other biologically active substance, for example, insulin. The hydrogel layer 12 contains a substance which reacts with or upon a substance in the surrounding environment. For example, the hydrogel 12 may contain glucose oxidase fixed to the hydrogel as in Example 7. If the device is in contact with the blood of a diabetic person and if the glucose level rises, as after a meal, more glucose will diffuse into the hydrogel layer 12 and will be acted upon by the glucose oxidase to produce gluconic acid which will in turn diffuse into the polymer 11 thereby reducing its pH and accelerating erosion of the polymer and release of insulin, which will counteract the effect of rising glucose level in the blood.

Figure 5:
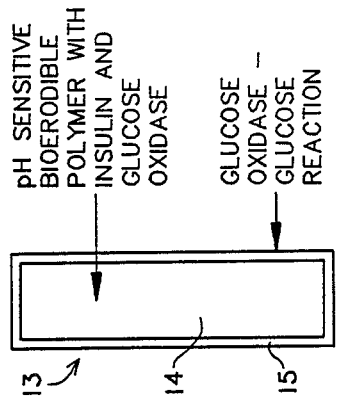

Referring now to FIG. 5, the entire device 13 consists of a body 14 of polymer of the invention containing a drug or other biologically active substance. Using insulin as an example of a drug, the polymer 14 will contain insulin and glucose oxidase. The surface layer 15 illustrates the initial zone of reaction. As the glucose level in the surrounding medium, e.g., circulating blood, glucose is converted to gluconic acid which by decreasing the pH increases the rate of erosion of the polymer and the rate of release of insulin.

GENERAL DISCUSSION

It will be apparent that considerable variation in the reactants and resulting polymers and in other aspects of the invention may be practiced. An amine group may be incorporated in the polymer in various ways. The amine groups may be primary, secondary or tertiary. Examples of amines are as follows:
Diethanol Amine
N,N-Dihydroxyethyl aniline
Methyl diethanol amine
Diethanol propanol amine
Butyldiethanol amine
Propyl diethanol amine
Isopropyl diethanol amine
Cyclohexyl diethanol amine
N-Benzyl-N,N-diethanol amine
3-Dimethylamino-1,2-propanediol
3-Diethyl amino-1,2-propanediol
1,3-Bis[tris(hydroxymethyl)methylamino]propane
2,2-Bis(hydroxymethyl)-2,2',2"-nitriloethanol
3-(tert-Butylamino)-1,2-propanediol
N-phenyl diethanol amine
Triethanol amine
Tris(hydroxymethyl)aminomethane
Dihydroxyethyl piparizine
Tri-isopropanol amine
7-(2,3-Dihydroxypropyl)theophylline
3,6-Dihydroxy pyridazine
2,3-Dihydroxy pyridine
2,4-Dihydroxy pyridine
2,6-Dihydroxy pyridine
4,6-Pyrimidinediol
N-Ethyl diethanol amine This list includes dihydroxy amines, trihydroxy amines, primary amines, secondary amines, and tertiary amines. The dihydroxy amines are preferably used as linking groups between the ketone acetal moieties, but they may be used to copolymerize with di- (or higher) ketene acetals, in the former case (diketene acetals) to form linear polymers. Preferably a dihydroxy amine is used to link the ketene acetal moieties and a tri- (or higher) hydroxy amine is used to cross link the resulting prepolymers.

In choosing an amine group, one may consider its basicity, the possible effects of substituents forming part of the amine group and the effect of other atoms and groups in the polymer such as steric effects.

In the formation of a prepolymer such as those of Examples 1, 2 and 3, a certain amount of the diol reactant (e.g. N-butyldiethanol amine of Example 1) may form small oligomers with the diketene acetal. However the amount of such small oligomers is not significant and the product, although it contains a small proportion of small oligomers, may be used without purification.

It will therefore be apparent that new and useful polymers, prepolymers, methods and fabricated products are provided.

We claim:

1. Bioerodible polymers capable of functioning as carriers of biologically active substances and release thereof by erosion of the polymer when brought into contact with an aqueous environment, said polymers containing in at least a substantial proportion of the polymer molecules an amine functionality such that the rate of erosion of the polymer in an acidic aqueous environment will increase as the pH of the environment diminishes.

2. The polymers of claim 1 which are poly(ortho esters) resulting from polymerization of a ketene acetal having a functionality of two or more with a polyol.

3. The polymers of claim 2 wherein the polymers are cross linked.

4. The polymers of claim 2 wherein the polymers are linear.

5. Polymers of claim 2 wherein the amine functionality is incorporated (1) in a group linking two molecules of a diketene acetal to produce a prepolymer diketene acetal, or (2) in the polyol or (3) in both the linking group and the polyol.

6. The polymers of claim 5 wherein the amine functionality is embodied in a secondary or tertiary amine group which is part of an open chain or a cyclic group or in a pendent primary, secondary or tertiary amine group.

7. Polymers having the repeating mer unit:

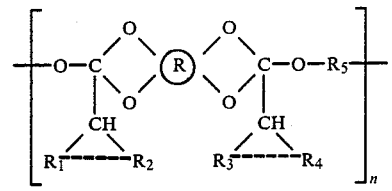

wherein n is an integer substantially greater than 10; wherein $R_1$ and $R_2$ are hydrogen or the same or different essentially hydrocarbon groups and may be separate groups or may form parts of a cyclic group: Ⓡ is a quadrivalent organic grouping; $R_3$ and $R_4$ are hydrogen or the same or different essentially hydrocarbon groups and may be separate groups or may form parts of a cyclic group; $R_5$ is an essentially hydrocarbon group which is the residue of a polyol $R_5(OH)_a$ wherein a is an integer equal to two or more, such polyol being a single molecular species or a mixture of molecular species; and wherein such linear chain may be crosslinked with other such chains, at least a substantial portion of the polymers having an amine functionality incorporated in the Ⓡ or in $R_5$ or in both, whereby the rate of erosion of the polymer in contact with an acidic aqueous medium is substantially greater at lower acidic pH's than at higher acidic pH's.

8. Polymers of claim 7 wherein the amine functionality is incorporated in Ⓡ.

9. Polymers of claim 7 wherein the amine functionality is incorporated in $R_5$.

10. Polymers of claim 7 wherein the amine functionality is incorporated in both Ⓡ and $R_5$.

11. Polymers of claim 7 wherein Ⓡ is the group

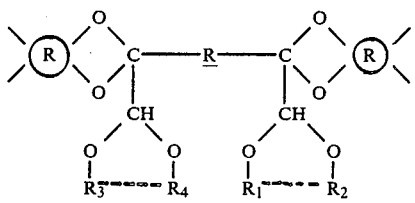

wherein R is a linking group and Ⓡ is a quadrivalent organic grouping.

12. Polymers of claim 11 wherein an amine functionality is incorporated in R.

13. Polymers of claim 11 wherein an amine functionality is incorporated in $R_5$.

14. Polymers of claim 11 wherein an amine functionality is incorporated in both Ⓡ and R5.

15. Compounds having the structure

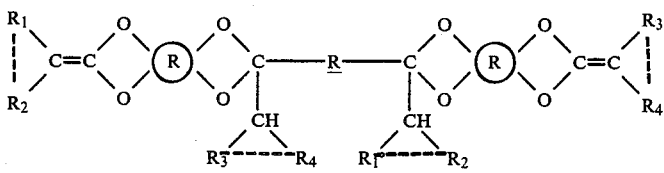

wherein $R_1$ and $R_2$ are hydrogen or the same or different essentially hydrocarbon groups and may be separate groups or may form parts of a cyclic group; Ⓡ is a quadrivalent organic grouping; $R_3$ and $R_4$ are hydrogen or the same or different essentially hydrocarbon groups and may be separate groups or may form parts of a cyclic group; and R is a linking group.

16. Compounds of claim 15 wherein R contains an amine group.

17. A method of producing biodegradable polymers which undergo faster erosion in an aqueous medium at lower acid pH's than at higher acid pH's, said method comprising copolymerizing at least two different monomeric species selected to produce a biodegradible polymer, at least one of such species containing an amine functionality.

18. The method of claim 17 wherein both species contain an amine functionality.

19. The method of claim 17 wherein one species is a ketene acetal having at least two ketene groups and the other species is a polyol.

20. The method of claim 19 wherein both the ketene acetal and the polyol contain an amine functionality.

21. The method of claim 19 wherein said ketene acetal has the structure

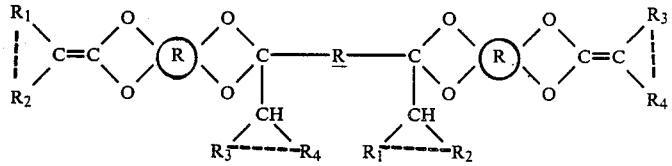

wherein $R_1$ and $R_2$ are hydrogen or the same or different essentially hydrocarbon groups and may be separate groups or may form parts of a cyclic group; Ⓡ is a quadrivalent organic grouping; $R_3$ and $R_4$ are hydrogen or the same or different essentially hydrocarbon groups and may be separate groups or may form parts of a cyclic group; and R is a linking group and the biologically active substance is premixed with said ketene acetal.

22. The method of claim 17 wherein the species are selected to cross link and the resulting product is a cross linked polymer.

23. The method of claim 22 wherein a biologically active substance is incorporated in one or the other or both species or in the mixture of the two prior to cross linking.

* * * * *